United States Patent
Groop et al.

(10) Patent No.: US 10,137,289 B2
(45) Date of Patent: *Nov. 27, 2018

(54) MICRONEEDLE CARTRIDGE AND NOSECONE ASSEMBLY

(71) Applicant: Esthetics Education LLC, Scottsdale, AZ (US)

(72) Inventors: Kristin Groop, Scottsdale, AZ (US); Lawrence G Groop, Scottsdale, AZ (US)

(73) Assignee: Esthetic Education LLC, Scottsdale, AZ (US)

( * ) Notice: Subject to any disclaimer, the term of this patent is extended or adjusted under 35 U.S.C. 154(b) by 82 days.

This patent is subject to a terminal disclaimer.

(21) Appl. No.: 15/424,871

(22) Filed: Feb. 5, 2017

(65) Prior Publication Data

US 2017/0173317 A1 Jun. 22, 2017

Related U.S. Application Data

(63) Continuation-in-part of application No. 14/975,718, filed on Dec. 19, 2015, now Pat. No. 10,010,708.

(51) Int. Cl.
*A61M 37/00* (2006.01)

(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/0046; A61M 5/20; A61M 5/46; A61M 5/24; A61M 5/28; A61M 2005/14252; A61M 2005/1585; A61M 2205/073

See application file for complete search history.

(56) References Cited

U.S. PATENT DOCUMENTS

| | | | | |
|---|---|---|---|---|
| 4,718,463 A | * | 1/1988 | Jurgens, Jr. | A61L 2/07 134/169 R |
| 5,507,795 A | * | 4/1996 | Chiang | A61B 17/32078 606/167 |
| 2002/0123675 A1 | * | 9/2002 | Trautman | A61B 17/205 600/309 |
| 2014/0121587 A1 | * | 5/2014 | Sallberg | A61N 1/0502 604/21 |

* cited by examiner

*Primary Examiner* — Nathan R Price
*Assistant Examiner* — Justin L Zamory
(74) *Attorney, Agent, or Firm* — Hartman Titus PLC; Joseph W Mott

(57) ABSTRACT

A microneedle cartridge is provided comprising a pair of concentric cylinders wherein an inner cylinder supports a microneedle array block and moves up and down an inside cylinder, driven by a central rod which connects the microneedle array to a drive motor. An inner baffle cylinder fits inside the inner cylinder and surrounds the central rod, isolating the microneedle array from the internal cavity of the machine. Fabric gaskets treated with antimicrobial solution are placed at the locations where the inner baffle cylinder meets the inner cylinder and where the inner cylinder meets the outer cylinder. A piston rod cradle at the bottom of the cartridge engages a cup-shaped polymer reciprocating piston rod that interacts with the device motor through a connecting metal piston. A removable, autoclavable metal nosecone covers the cartridge assembly.

5 Claims, 7 Drawing Sheets

MICRONEEDLE CARTRIDGE AND NOSECONE ASSEMBLY

CROSS REFERENCE TO RELATED APPLICATIONS

Figure 1:
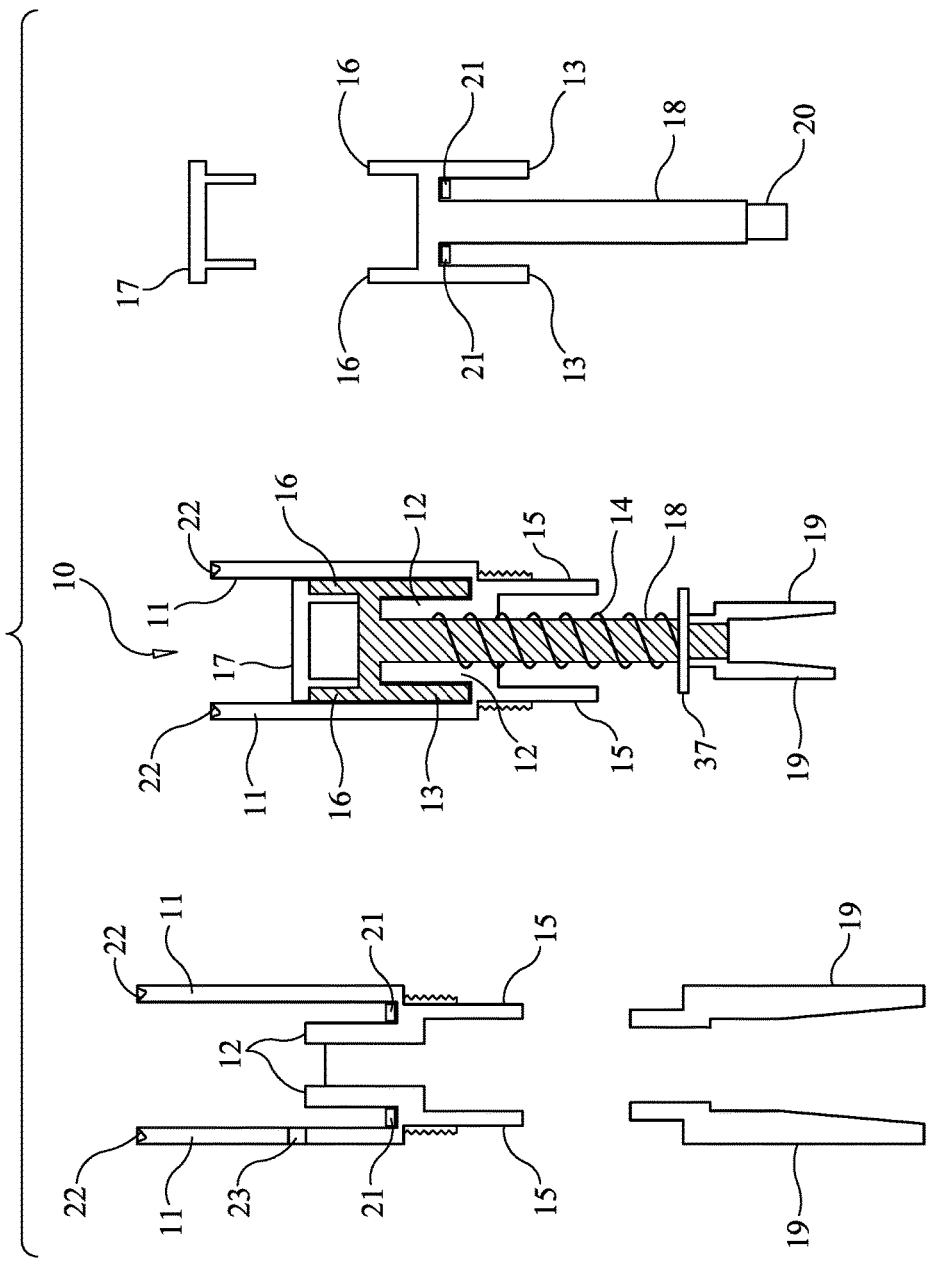

This application is a continuation in part of U.S. application Ser. No. 14/975,718, filed Dec. 19, 2015 (now U.S. Pat. No. 10,010,708), which claims the benefit of U.S. provisional patent application 62/094,965, filed Dec. 20, 2014.

TECHNICAL FIELD OF THE INVENTION

The present device components relate in general to a skin treatment protocol and, more particularly, to an apparatus, a system, and a method to deliver beneficial molecules in order to enhance the appearance of the skin while, simultaneously, prohibiting any liquid, bodily fluid, or topical product from entering into the apparatus.

BACKGROUND OF THE INVENTION

In modern society, much importance has been placed on physical appearance. The relative condition of a person's skin often implies health, youth, and beauty. Dermatological conditions such as acne scarring, stretch marks, surgical scars, melasma, and other conditions detract from the appearance of the skin. There has been much attention and research devoted to beautifying the skin.

The skin comprises the largest organ in the body and as a semi-permeable membrane, provides protection from most elements of the outside environment while also allowing the exchange of oxygen, water, and smaller molecules. The three layers of the skin from superficial to deep are the epidermis, the dermis, and the subcutaneous layer.

The epidermis is comprised of several layers of cells called keratinocytes. The deepest layer of the epidermis is called the basal layer and is comprised of living keratinocytes that both proliferate and differentiate into more specialized keratinocytes called corneocytes. These processes of keratinocytes replicating and turning into dead corneocytes allows the skin to continuously shed its outer layer and replenish the integrity of the skin. The most superficial layer of the skin which contains the corneocytes is the stratum corneum.

The stratum corneum is an effective barrier to many substances. At the molecular level, the stratum corneum's multiple layers of corneocytes prevent larger molecules from crossing it. With respect to beautification treatments, many of the compounds described through marketing as being beneficial to some structure(s) residing below the dead stratum corneum do not actually make it past the stratum corneum and thus cannot act on deeper structures.

Significant research has been performed to determine what characteristics allow a particular molecule to pass through the stratum corneum. Many researchers cite that among all molecular characteristics, the size of the molecule (measured in Daltons) is the single most important factor in determining whether or not a molecule may pass through the epidermis. Several researchers have shown that the stratum corneum has the ability to prevent the transmission of any molecule over 500 daltons without the aid of some enhancement or stratum corneum bypass technology. Vitamin C, for example, has a mass/size of 176 daltons and readily crosses the stratum corneum.

There are thousands of treatment protocols aimed at beautifying the skin and mitigating the appearance of dermatological conditions. Manufacturers of cosmetics market topical creams, liquids, and lotions that are purported to beautify the skin. Many of these are described as having the ability to penetrate deeply into the skin and perform functions such as aid in reversing the aging process or fight free radicals, and many other dubious claims. However, as described above, unless the molecule is under 500 daltons or is aided by a stratum corneum bypass technique, many of these "miracle creams" simply do not pass the stratum corneum. It is important to recognize that the stratum corneum itself, can and does benefit from certain topicals. However, because the stratum corneum is not a living layer of tissue, any claim involving biologically active cells or functions cannot be true.

Skin professionals ranging from doctors to estheticians have developed techniques designed to penetrate, remove, or bypass the stratum corneum and/or deeper layers of the epidermis. Some of these treatment protocols were designed specifically to allow molecules, which normally could not cross the stratum corneum, to penetrate into the dermis. One set of techniques involve the use of penetrating the skin with tiny, solid, sterile, microneedles. These techniques create microchannels that, for a short period of time, allow molecules larger than 500 daltons to cross the stratum corneum. Depending on the relative depth of the microneedles, some practitioners intentionally microneedle the skin for the additional reason of inflicting tiny microinjuries into the dermis that stimulate the body's cutaneous wound response to remodel the dermal tissues in an effort to beautify the skin. Microneedling to a depth that reaches the dermis allows the microneedles to come into contact with blood and bodily fluids. In both cases, many of these treatment protocols involve the use of liquid or cream topicals being applied before, during, and after the microneedling of the skin. Some practitioners employ a more complex protocol which involves removing a volume of blood from the patient via a hypodermic syringe, separating the blood products by means of a centrifuge, adding a chemical agent to the isolated platelet volume extracted, and then applying the activated platelet isolate to the skin before and/or during the microneedling of the skin.

There have been several devices invented all of which rely on the use of tiny microneedles which penetrate the skin. Some of these devices are designed to allow an electric motor housed inside a handheld stylus to attach to a disposable plastic cartridge that has an array of tiny microneedles affixed to the non-attached end. Many of these motorized devices allow the practitioner to adjust both the depth of penetration into the skin as well as the speed in which the motor reciprocally propels and withdraws the microneedle array.

There are various microneedle cartridge designs. Virtually all microneedle cartridges rely on a plastic outer cartridge cylinder to attach to the motorized device, house the internal components, provide the support and structure to direct the path and motion of the microneedles, and provide some measure of protection from accidentally coming into contact with the sharp microneedle array. Virtually all microneedle cartridges rely on a single plastic or metal central rod which attaches or otherwise engages the reciprocal piston rod of the electric motor on one end and has a microneedle array comprised of a differing number and arrangement of microneedles on the other end. Most microneedle designs incorporate a spring mechanism that surrounds the central rod and assists with the withdrawal stroke of the microneedles from the skin. The spring mechanisms currently employed are either a metal coil design or an accordion corrugated silicon/plastic design.

Currently, microneedle cartridges attach to a fixed, non-removable nose cone apparatus by various threaded or slotted adaptations on both the microneedle cartridge and the nose cone apparatus. The microneedle cartridges are designed to be opened from sterile packaging, affixed to the nose cone, used on the patient, removed from the nose cone, and then disposed of in a safe container.

Currently, the design of microneedling cartridges utilizing a metal coil spring mechanism allow topical and bodily fluids to enter into the cartridge via the gap between the outer cartridge wall and the inner microneedle array block. These fluids then travel towards and enter into the motorized microneedling device via the gap between the outer cartridge connection to the motorized device and the central rod affixing the microneedling array. Based on current designs, both of these gaps were necessary to allow the internal central rod with the microneedle array to freely reciprocate inside the outer plastic housing cylinder. Fluid movement through the cartridge is facilitated by the suction pressure created by the reciprocal action of the microneedle array which is, in effect, sealed to the skin via the outer plastic cylinder housing being pressed against moist skin during the treatment. Additionally, capillary action facilitates movement of fluid through the microneedle cartridge.

Currently, all motorized microneedling devices are not able to be dry or steam autoclave sterilized as the electrical components cannot be removed and would be destroyed in the autoclave. This poses a cross contamination problem to both patient and practitioner as all current motorized microneedle devices only allow the practitioner to attempt to remove the topical and bodily fluids that have entered the motorized device nose cone by the use of liquid disinfectants such as isopropyl alcohol. Indeed, many manufacturers specifically direct practitioners to either dip the nose cone into alcohol or use an alcohol soaked cotton swab to clean the nose cone of the motorized microneedling device.

The Center for Disease Control and many other entities such as the American Medical Association cite that the only methods to effectively sterilize a surgical instrument that comes into contact with bodily fluids are properly performed dry heat sterilization, steam sterilization or chemical gas sterilization. The use of disinfectants, even high level disinfectants, cannot adequately kill pathogens derived from bodily fluids.

Even though the current microneedle cartridges are single use and disposable, the bodily fluids that leak into the nose cone apparatus of the motorized microneedling device cannot be effectively removed and decontaminated from pathogens because the devices, as they are designed now, cannot be sterilized. These pathogens remain inside the nose cone section of the microneedling pen and, in some cases for certain motorized microneedling device designs, inside the motor chamber. Once inside, these pathogens can potentially multiply. When the next microneedle cartridge is inserted and the device is used on the next patient, the bodily fluids from the new patient may come in contact with the bodily fluid residue trapped inside the motorized microneedling device potentially allowing transmission of pathogens to the new patient.

Microneedle cartridge manufacturers have attempted to mitigate the cross contamination issue by replacing the metal spring with an accordion corrugated silicon spring that provides some assistance with removing the microneedles from the skin during the withdrawal stroke while also acting as a gasket to attempt to seal the gap between the outer cartridge connection to the motorized device and the central rod affixing the microneedling array. However, these silicon based springs are not as effective in assisting the withdrawal stroke as are metal springs. As a result of the device being inefficient in removing the needles on the withdrawal stroke, especially at greater depths of penetration, more power is required of the motor. Once the motor has reached its maximum power output, the inefficiency of the silicon spring against the increased friction of the skin against the microneedle array at greater depths of penetration causes the microneedle array to drag in the skin, tearing it. Additionally, the life of the motor is significantly shortened.

Other approaches to mitigate cross contamination include the addition of a small hole in the outer cartridge cylinder wall to minimize suction. One manufacturer has developed a plastic perforated outer plastic guide that contacts the skin guiding the needles to go through narrow, aligned channels which reduces the amount of fluids that can reach the gap between the outer cartridge wall and the inner microneedle array. However, this device utilizes a metal spring with the gap between the outer cartridge connection to the motorized device and the central rod affixing the microneedling array. Both of these designs have been shown to reduce, but not completely eliminate, the chances of bodily fluids entering the motorized microneedling device.

In summary, as they are designed now, motorized microneedling devices as well as the microneedling cartridges attached to them allow bodily fluids (including blood) to enter the motorized microneedling nose cone. Once inside, the device cannot be sterilized increasing the risk of transmitting blood borne pathogens from patient to patient.

SUMMARY OF THE INVENTION

Based on the health risks posed to patients by virtue of possible exposure to blood borne pathogens trapped inside the motorized microneedling device and then potentially transmitted to the next patient, it is apparent that current motorized microneedling devices are not capable of preventing fluids from exiting the needle cartridge and entering the device. In order to prevent this, a new cartridge and nose cone assembly system is presented. Three features are combined into a microneedling cartridge interface that prevents the transmission of any fluid from microneedle cartridge into the motorized microneedling device as well as affording the ability to remove and autoclave sterilize the portion of the motorized microneedling device in contact with the microneedle cartridge. Additionally, a polymer reciprocal piston rod affords the ability to provide an adequate connection to the microneedle cartridge receiver while also allowing the polymer reciprocal piston rod to be replaced in the event of damage or wear. The microneedle cartridge apparatus is constructed with two internal baffle cylinders and two absorbent gaskets that prevent any liquid from traveling from the gap between the outer cartridge wall and the inner microneedle array block, through the cartridge and into the motorized microneedling device via the gap between the outer cartridge connection to the motorized device and the central rod affixing the microneedling array. These absorbent gaskets prevent capillary action from facilitating the travel of liquid through the microneedle cartridge and are treated with an antimicrobial agent to marginalize any pathogen coming into contact with the gaskets. Currently, there are no other microneedle cartridges incorporating the use of absorbent material to trap liquids. One inner concentric cylinder slides inside a tightly machined gap between the outer cylinder allowing the central rod with the microneedle array attached to move freely through the outer cartridge connection housing while simultaneously preventing liquids from traversing the gap between them as they are arranged with the height of the smaller central cylinder being greater than the distance traveled outwards into the skin by the central rod attached to the microneedle array. In this way the path through the microneedle cartridge is comprised of two 180 degree turns with absorbent material gaskets at each turn to absorb any liquid that could possibly travel this path. The microneedle cartridge itself is attached to the nose cone of the motorized microneedling device by means of male to female threads. As the microneedle cartridge was designed to prevent fluids from being able to enter the motorized microneedling device, this microneedle cartridge is able to safely utilize a stiff metal return spring maximizing the depth the microneedle array can efficiently enter and withdraw from the skin without tearing it or damaging the electric motor. In order to provide another backup system to further prevent liquids from entering the motor area of the microneedle device, a thin silicone gasket is attached on the end of the central rod of the microneedle cartridge very close to where it connects with the polymer reciprocal piston rod. This junction is where the microneedle cartridge is attached to the motorized microneedling device.

To complete the microneedle cartridge interface system, the nose cone section of the motorized microneedling device is able to be removed from the rest of the device by means of male to female threads. While the absorbent gaskets, concentric cylinders and restricted path for liquids incorporated into the design of microneedle cartridge prevents liquids from entering the nosecone section from the microneedle array, in the event any liquids could somehow enter the nosecone, the nose cone can be removed, autoclaved sterilized, and replaced prior to the next patient. The removable nose cone is designed with a tight gap tolerance between the nose cone central opening and the reciprocal piston rod of the microneedling device to effectively contain and isolate within itself, any particulate or liquid that may somehow enter the nose cone. By closely adapting the shape of the connecting end of the reciprocal piston rod to the piston rod housing, the ability for liquid or particulate matter to enter the piston rod housing is significantly reduced. By constructing the reciprocal piston rod out of dense polymer or some equivalent material, it is able to provide a secure connection between the receiver end of the microneedle cartridge and the polymer reciprocal piston rod. This is facilitated by the addition of ribbed grooves stamped into the receiver cradle of the microneedle cartridge apparatus. Unlike many metal or plastic reciprocal piston rods, this polymer reciprocal polymer reciprocal piston rod is not a traditional rod shape but, rather, is a cup shaped disk that provides a floor and walls that closely adapt to the device housing. As this rod is actually shaped as a cup, this provides yet another barrier for any liquid or particulate to enter the device. Additionally, the polymer reciprocal piston rod can easily be replaced if it becomes worn or damaged. In order to facilitate patient efficiency and the time necessary to autoclave sterilize the nose cone, multiple nose cones are provided with each system so that the operator has access to a sterile nosecone while the previously used nosecone is being sterilized.

Together, as one microneedle cartridge interface system, the twin baffle cylinders microneedle cartridge apparatus with fabric gaskets, the removable, autoclavable, nose cone apparatus and the closely adapted polymer reciprocal, cup-shaped piston rod apparatus, as well as the connection gasket, provide the operator the ability to safely microneedle a patient by greatly reducing the chance of cross-contamination, autoclave the portion of the device that comes into contact with the microneedle cartridge, and easily replace a worn or damaged reciprocal piston rod.

BRIEF DESCRIPTIONS OF THE DRAWINGS

To provide a more complete understanding of the present invention and features and advantages thereof, reference is made to the following description, taken in conjunction with the accompanying figures, wherein like reference numerals represent like parts, in which:

FIG. 1 is a schematic diagram illustrating the components, arrangement and assembly of an embodiment of the microneedle cartridge apparatus.

FIG. 2 is a simplified isometric projection illustrating the female connection threads of the outer cartridge connection cylinder.

FIG. 3 is a 3D frontal projection illustrating the nose cone apparatus and the reciprocal piston rod apparatus in accordance with one embodiment of the present invention.

FIG. 4 illustrates the cup shaped reciprocal piston rod apparatus.

FIG. 5 is a cut away isometric projection illustrating the arrangement of the containment cylinders inside the microneedle cartridge housing.

FIG. 6 is a schematic of a microneedle device adapted to use an embodiment of the present invention.

FIG. 7 is a schematic diagram illustrating the components, arrangement and assembly of another embodiment of the microneedle cartridge apparatus.

FIG. 8 is a 3D frontal projection illustrating the nose cone apparatus and the reciprocal piston housing in a different embodiment of the present invention FIG. 9 illustrates the inverted cylinder reciprocal piston rod apparatus.

FIG. 10 is a cut away isometric projection illustrating the arrangement of the containment cylinders inside the microneedle cartridge housing in another embodiment.

DETAILED DESCRIPTION OF EXAMPLE EMBODIMENTS

FIG. 6 illustrates the general configuration of a microneedling pen or microneedling device adapted to employ the present invention. Microneedling device body 40 contains a power source, an electric motor moving a high speed reciprocating piston, and speed and depth controls. Microneedling cartridge 10 comprises an embodiment of the present invention. Nosecone 30 joins the device body 40 and the cartridge 10.

FIG. 1 is a schematic diagram illustrating the components and assembly of the microneedle cartridge apparatus 10 designed to prevent the transmission of bodily fluids in accordance with one embodiment of the present invention. The central figure shows the cartridge apparatus, with some of the components broken out and repeated on the left and right figures. Microneedle cartridge apparatus 10 includes outer cartridge cylinder 11, which provides support and isolation for internal components. Attached to, and contiguous with outer cartridge cylinder 11 is inner baffle cylinder 12, which is smaller than and is positioned between outer cartridge cylinder 11 and outer baffle cylinder 13. Outer baffle cylinder 13 is attached to and contiguous with central rod 18. Additionally, attachment cradle 16 is contiguous with, and is a superior extension of outer baffle cylinder 13. Cylinders 12 and 13 are machined to a tight tolerance to allow reciprocal movement of outer baffle cylinder 13 (connected to central rod 18) between outer cartridge cylinder 11 and inner baffle cylinder 12. As outer baffle cylinder 13 is reciprocating between outer cartridge cylinder 11 and inner baffle cylinder 12, liquids cannot potentially squeeze between the tops of inner baffle cylinder 12 and outer baffle cylinder 13 as the height of inner baffle cylinder 12 is at least 2 mm greater than the distance the inferior edge of outer baffle cylinder 13 travels superiorly towards the patient. Additionally, any liquid that may have just entered the microneedle cartridge apparatus 10 must first come into contact with absorbent gasket 21 prior to traveling towards the interface between inner baffle cylinder 12 and outer baffle cylinder 12 and would be absorbed by absorbent gasket 21. This arrangement creates a tortuous path including two 180 degree turns for any liquids that enter the microneedle cartridge during treatment. This convoluted path prevents liquids from traversing through the microneedle cartridge apparatus into the nose cone apparatus and deeper into the polymer reciprocal piston rod chamber.

Microneedle cartridge apparatus 10 also includes metal return spring 14, which assists the microneedle array retraction from the skin during the withdrawal stroke of the reciprocal action provided by the motorized microneedle device. As the microneedle cartridge was designed to prevent fluids from being able to enter the motorized microneedling device, this microneedle cartridge is able to safely utilize stiff metal return spring 14, instead of an inefficient silicon accordion spring allowing 14 to maximizing the depth the microneedle array can efficiently enter and withdraw from the skin without tearing it or damaging the electric motor.

Figure 6:
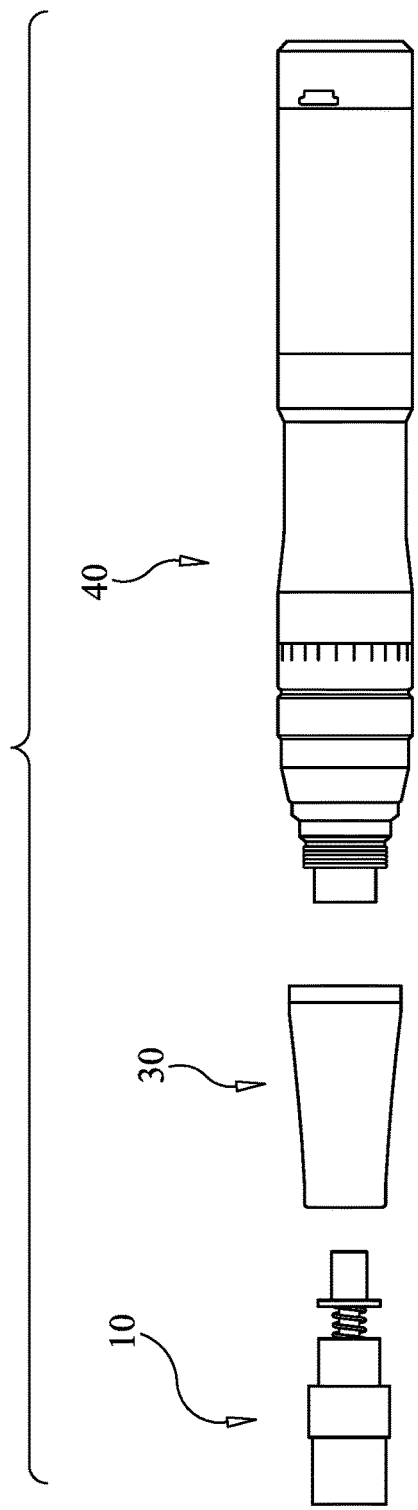

Microneedle cartridge apparatus 10 also includes the female threaded outer cartridge insertion cylinder 15, which attaches the microneedle cartridge apparatus 10, to the nose cone apparatus (later designated as 30 in FIGS. 3 and 6).

Microneedle cartridge apparatus 10 also includes microneedle array attachment cradle 16. Attachment cradle 16 is contiguous with and connected to as an extension of outer baffle cylinder 13. Attachment cradle 16 attaches to the microneedle array 17. Microneedle array 17 has several forms in which various numbers of various lengths of microneedles are arranged.

Configuring microneedle cartridge apparatus 10 with the ability to interchange different variants of microneedle array 17, affords the ability for different treatment protocols such as using a larger array with more microneedles for larger treatment areas. Thus, microneedle cartridge apparatus 10 can be modified during manufacturing assembly to provide the skin care professional with a wide range of treatment possibilities.

Microneedle cartridge apparatus 10 also includes central rod 18, which travels through a central opening in outer cartridge cylinder 11 connecting both the microneedle array attachment cradle 16 and outer baffle cylinder 13 to the reciprocal piston rod attachment cradle 19 via the circumferentially reduced connection rod end 20. Reciprocal piston rod attachment cradle 19 attaches to reciprocal piston rod (later designated as 31 in FIG. 3). Unlike a traditional attachment cradle, reciprocal piston rod attachment cradle 19 is designed to be the female receiver. While microneedle cartridge apparatus 10 is designed to prevent liquid from exiting the cartridge, the female receiver shape of 19 is different from other devices as it further reduces the potential for any liquid entering the gap between the piston rod and the piston rod chamber that is present in several device designs (including this one). Specifically, by designing the connection between the piston rod and the central rod as having reciprocal piston rod attachment cradle 19 as the female connection that is facing the opposite direction as the path of any liquid exiting the gap between the central rod 18 and the central opening in outer cartridge cylinder 11, the potential for liquid to enter the gap between the piston rod and piston rod chamber is minimized. In addition, access to this gap is reduced by the shape of the female polymer reciprocal piston rod attachment cradle 19 acting as an umbrella or shroud forcing any liquid or particulate to the outside of the cylinder away from the gap. In an additional effort to reduce the potential chance for liquids to enter the gap between the piston rod and piston rod chamber, a silicon connection gasket 37, is slid onto central rod 18 just above female polymer reciprocal piston rod attachment cradle 19. Silicon connection gasket 37 acts to extend the umbrella shaped protection of female polymer reciprocal piston rod attachment cradle 19 by providing a flexible gasket to minimize the gap between the piston rod and piston rod chamber.

Microneedle cartridge apparatus 10 also includes absorbent material gaskets 21, which absorb any liquid that might enter the cartridge and attempt to travel through the microneedle cartridge apparatus via capillary action or suction. Absorbent material gasket 21 has been treated with an anti-microbial solution to further marginalize potential pathogens that might enter. Microneedle cartridge apparatus 10 also includes scalloped edge 22 on outer cartridge cylinder as well as suction relief opening 23, which together with scalloped edge 22, reduces any suction that might develop from the operation of the motorized microneedle device microneedle cartridge apparatus against moist skin. These design enhancements further prevent the potential transmission of blood borne pathogens via cross contamination by virtue of bodily fluids entering the nose cone apparatus during operation.

Figure 2:
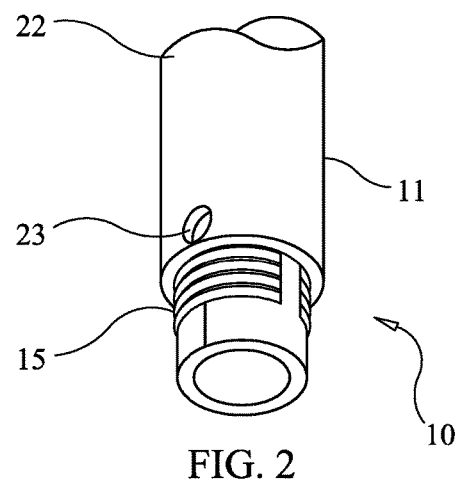

FIG. 2 is a simplified isometric projection further illustrating microneedle cartridge 10. Microneedle cartridge apparatus 10 includes outer cartridge cylinder 11, which provides support and isolation for internal components. Microneedle cartridge apparatus 10 also includes the female threaded outer cartridge insertion cylinder 15, which attaches the microneedle cartridge apparatus 10, to the nose cone apparatus (not depicted). FIG. 2 illustrates a different angle of scalloped edge 22 on outer cartridge cylinder 11 as well as suction relief opening 23, which together with scalloped edge 22, reduces any suction that might develop from the operation of the motorized microneedle device microneedle cartridge apparatus against moist skin.

Figure 3:
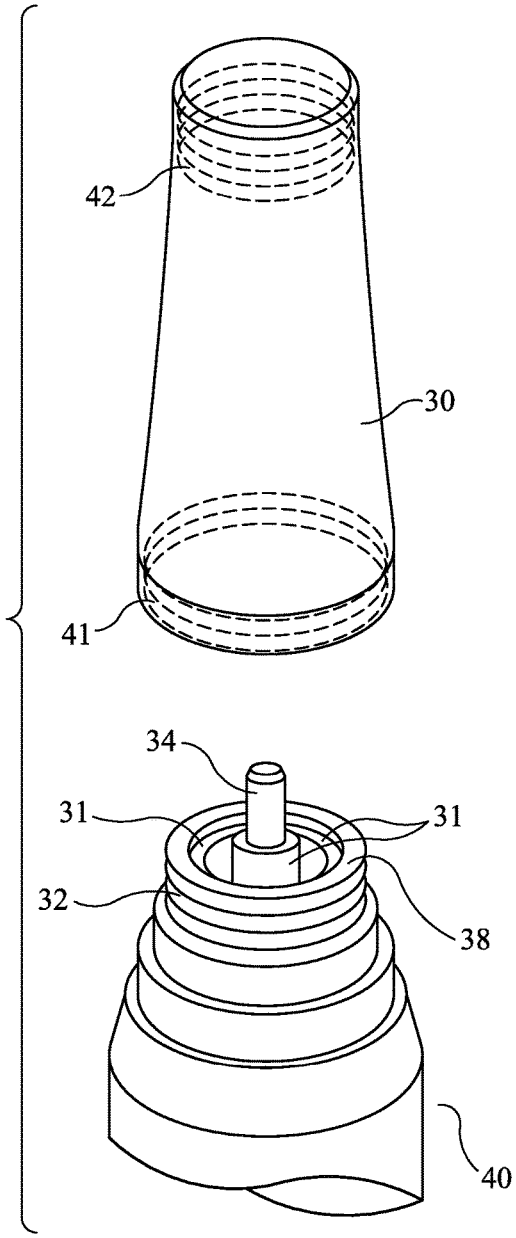

FIG. 3 is an isometric frontal projection illustrating removable nose cone apparatus 30, which has female threading 41 at its proximal end to match threading 32 of the microneedle device housing 40, and female threading 42 at its distal end to match threading 15 of microneedle cartridge 10. This allows the operator to remove it by unscrewing it from the external (male) connection threads 32 of the microneedle device housing 40. In an embodiment, the aluminum nose cone apparatus 30 can be autoclaved sterilized. In order to eliminate waiting the time necessary for the nose cone apparatus 30 to be sterilized during the autoclave cycle, multiple nose cone apparatuses may be provided with the system. In this way, the operator can unscrew, remove and discard the microneedle cartridge apparatus 10, and then unscrew and remove the nose cone apparatus 30. Once the unsterilized nose cone apparatus 30 has been removed, a different, sterilized, nose cone apparatus 30 can be affixed to the device. Nose cone apparatus 30 is designed with tight tolerances between the central rod 18 and itself. This design feature is yet another safeguard to further reduce the potential for cross-contamination.

Additionally, FIG. 3 also depicts the cup shaped reciprocal piston rod 31, which has been designed to allow a secure connection between it and reciprocal piston rod attachment cradle 19 while allowing the entire microneedle cartridge apparatus 10 to be screwed onto nose cone apparatus 30 via male to female threads without damaging cradle 19.

The design of reciprocal piston rod 31 also includes another safeguard to further reduce the ability of any liquid or particulate from entering the gap between the rod 31 itself and the reciprocal piston rod housing 38. This is accomplished by minimizing this gap with close tolerances between 31 and 38 and more importantly, designing the reciprocal piston rod 31 as a cup shaped cylinder that provides a floor and walls that closely adapt to the reciprocal piston rod housing. On FIG. 3, the cup shaped reciprocal piston rod 31 has three arrows pointing to its center cylinder as well as the cylinders outside edges. Piston rod attachment spindle 34 is immediately superior to the center cylinder of polymer reciprocal piston rod 31. As rod 31 is actually shaped as a cup, this provides yet another barrier for any liquid or particulate to enter the polymer reciprocal piston housing 38. Additionally, reciprocal piston rod 31 threads onto a metal reciprocal piston 35 (illustrated in FIG. 4) attached to the metal reciprocal piston attachment cradle 36. (illustrated in FIG. 4). As reciprocal piston rod 31 can be manufactured to fit to any size metal reciprocal piston, the disclosed apparatus has the capacity to be adapted to existing microneedle motor assemblies. This ability also allows polymer reciprocal piston rod 31 to be easily removed and replaced in the event of damage or wear.

Figure 4:
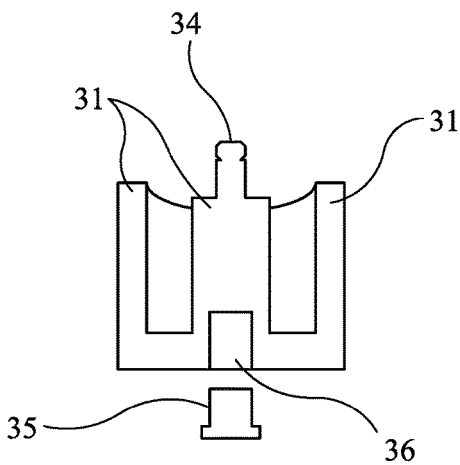

FIG. 4 is a simple cut away isometric projection illustrating cup shaped reciprocal piston rod 31. Piston rod attachment spindle 34 is immediately superior to the center cylinder of reciprocal piston rod 31. As rod 31 is actually shaped as a cup, this provides yet another barrier for any liquid or particulate to enter the reciprocal piston housing 38. Additionally, reciprocal piston rod 31 threads onto a metal reciprocal piston 35 attached to the metal reciprocal piston attachment cradle 36. In the event reciprocal piston rod 31 needs to be removed and replaced in the event of damage or wear, it can be easily unscrewed from metal reciprocal piston 35.

Figure 5:
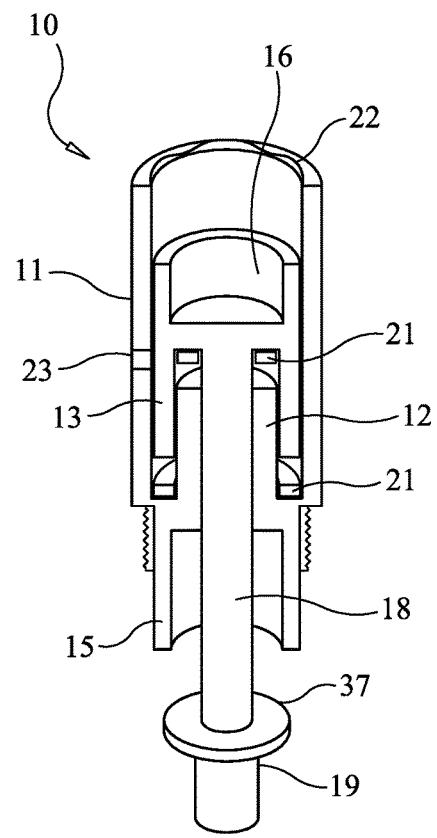

FIG. 5 is a cut away isometric projection diagram illustrating the components and assembly of the microneedle cartridge apparatus 10 designed to prevent the transmission of bodily fluids in accordance with one embodiment of the present invention. Microneedle cartridge apparatus 10 includes outer cartridge cylinder 11, which provides support and isolation for internal components. Attached to, and contiguous with outer cartridge cylinder 11 is inner baffle cylinder 12, which is smaller than and is positioned between outer cartridge cylinder 11 and outer baffle cylinder 13. Outer baffle cylinder 13 is attached to and contiguous with central rod 18. Additionally, attachment cradle 16 is contiguous with, and is a superior extension of outer baffle cylinder 13. Cylinders 12 and 13 are machined to a tight tolerance to allow reciprocal movement of outer baffle cylinder 13 between outer cartridge cylinder 11 and inner baffle cylinder 12. This arrangement allows for only one path for liquids to travel through the microneedle cartridge apparatus 10. Liquid must move down between outer cartridge cylinder 11 and outer baffle cylinder 13, then upward between outer baffle cylinder 13 and inner baffle cylinder 12, then downward between inner baffle cylinder 12 and central rod 18. This path includes two 180 degree turns that interface directly with absorbent material gasket 21 at each turn, and this convoluted path prevents liquids from traversing through the microneedle cartridge apparatus into the nose cone apparatus and deeper into the reciprocal piston rod chamber.

Figure 7:
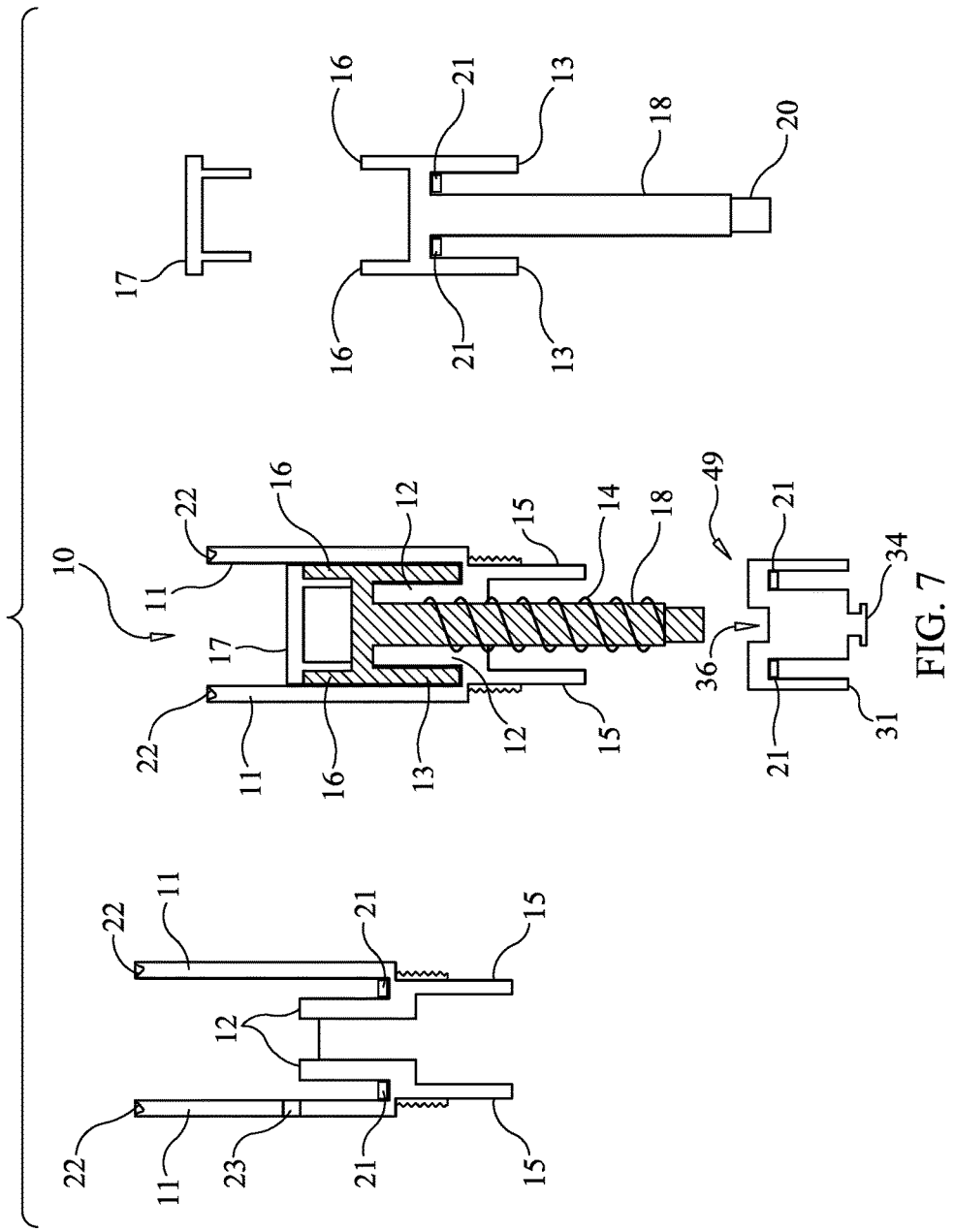

FIG. 7 is a schematic diagram illustrating a different embodiment. The components and assembly of the microneedle cartridge apparatus 10 are the same as the components described above and illustrated in FIG. 1, except that reciprocal piston rod attachment cradle 19 is replaced by inverted cylinder reciprocal piston rod attachment cradle 49. Unlike a traditional attachment cradle, reciprocal piston rod attachment cradle 49 is designed to cover the reciprocal piston housing 38. While microneedle cartridge apparatus 10 is designed to prevent liquid from exiting the cartridge via the gap between the central rod 18 and the central opening in outer cartridge cylinder 11, the inverted cylinder incorporated into reciprocal piston rod attachment cradle 49 is different from other devices as it further reduces the potential for any liquid entering the reciprocal piston housing 38 that is present in several device designs. Specifically, by configuring reciprocal piston rod attachment cradle 49 as an inverted cylinder that covers the reciprocal pistol housing, the interconnection between the reciprocal piston rod attachment cradle 49 and the reciprocal piston housing 38 faces in the opposite direction from the path of any liquid exiting the gap between the central rod 18 and the central opening in outer cartridge cylinder 11. Consequently, the potential for liquid to enter the gap between the piston rod and piston rod chamber is minimized. In addition, access to this gap is reduced by the shape of the inverted cylinder reciprocal piston rod attachment cradle 49 acting as an umbrella or shroud forcing any liquid or particulate to the outside of the reciprocal piston housing and away from the only entrance to the motor assembly. To further deter liquids from entering the reciprocal piston housing 38, the three sided circular channel created by the floor and walls of the reciprocal piston rod cradle 49 that comes into contact with the distal edge of the reciprocal piston housing has an absorbent material gasket 21 present. In an additional effort to reduce the potential chance for liquids to enter the gap between the piston rod and piston rod chamber, a silicon connection gasket 37, is slid onto central rod 18 just above inverted cylinder reciprocal piston rod attachment cradle 49. Silicon connection gasket 37 (seen in FIG. 10) acts to extend the umbrella shaped protection of inverted cylinder reciprocal piston rod attachment cradle 49 by providing a flexible gasket to act as an additional means to block liquids from coming into contact with the gap between the piston rod and piston rod chamber.

Figure 8:
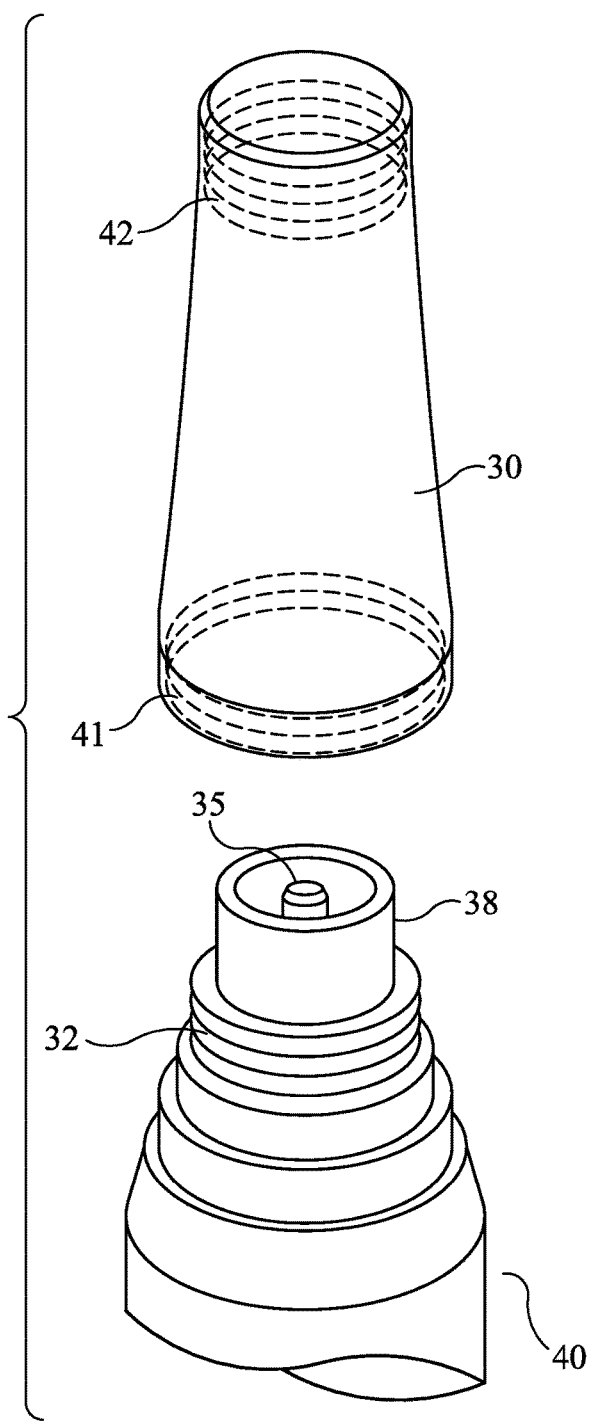

FIG. 8 is an isometric frontal projection illustrating removable nose cone apparatus 30, which has female threading 41 at its proximal end to match threading 32 of the microneedle device housing 40, and female threading 42 at its distal end to match threading 15 of microneedle cartridge 10. This allows the operator to remove it by unscrewing it from the external (male) connection threads 32 of the microneedle device housing 40. In an embodiment, the aluminum nose cone apparatus 30 can be autoclaved sterilized. In order to eliminate waiting the time necessary for the nose cone apparatus 30 to be sterilized during the autoclave cycle, multiple nose cone apparatuses may be provided with the system. In this way, the operator can unscrew, remove and discard the microneedle cartridge apparatus 10, and then unscrew and remove the nosecone apparatus 30. Once the unsterilized nose cone apparatus 30 has been removed, a different, sterilized, nose cone apparatus 30 can be affixed to the device. Nose cone apparatus 30 is designed with tight tolerances between reciprocal piston housing 38 and itself. This design feature is yet another safeguard to further reduce the potential for cross-contamination. FIG. 8 also depicts female T-shaped receiver cradle 35 located in the center of reciprocal piston housing 38 and connected to motor arm (not pictured) inside microneedle device housing 40. Different embodiments include different shaped receiver cradles 35 to match the particular shape of the male piston rod attachment spindles that are used in a particular embodiment.

Figure 9:
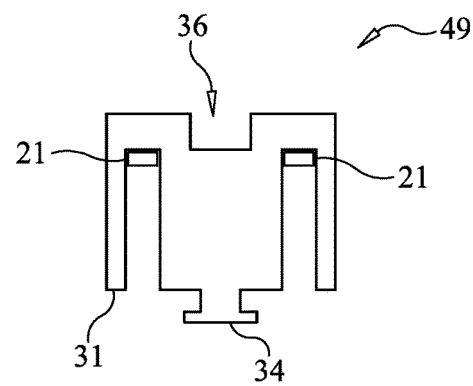

FIG. 9 is a simple cut away illustrating the cup shaped reciprocal piston rod attachment cradle 49, which has been designed to allow a secure connection between it and the circumferentially reduced connection rod end 20.

In FIG. 9 the design of reciprocal piston rod attachment cradle 49 also includes another safeguard to further reduce the ability of any liquid or particulate from entering the reciprocal piston housing 38. This is accomplished by covering reciprocal piston housing 38 with piston housing cover cylinder 31 and minimizing the gap with close tolerances between 31 and 38 and, more importantly, designing the piston housing cover cylinder 31 as an inverted cup shaped cylinder that provides a ceiling and walls that closely adapt to the reciprocal piston housing 38. T-shaped male piston rod attachment spindle 34 is immediately inferior to the center cylinder of polymer piston housing cover cylinder 31 and attaches to the female T-shaped receiver cradle 35 (shown in FIG. 8) Additionally, circumferentially reduced connection rod end 20 is glued into connection rod attachment cradle 36. To further deter liquids from entering the reciprocal piston housing 38, the three sided circular channel created by the floor and walls of the reciprocal piston rod cradle 49 that comes into contact with the distal edge of the reciprocal piston housing has an absorbent material gasket 21 present. As piston housing cover cylinder 31 can be manufactured to fit to any size reciprocal piston housing 38, the disclosed apparatus has the capacity to be adapted to existing microneedle motor assemblies.

Figure 10:
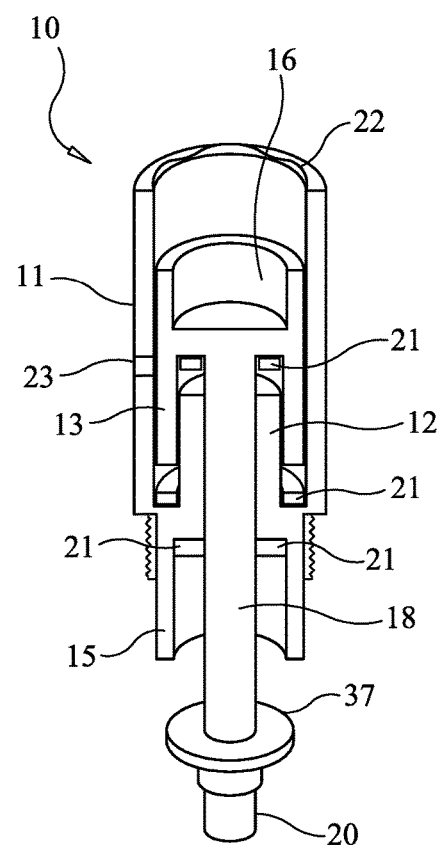

FIG. 10 is a cut away isometric projection diagram illustrating the components and assembly of the microneedle cartridge apparatus 10 designed to prevent the transmission of bodily fluids in accordance with one embodiment of the present invention. Microneedle cartridge apparatus 10 includes outer cartridge cylinder 11, which provides support and isolation for internal components. Attached to, and contiguous with outer cartridge cylinder 11 is inner baffle cylinder 12, which is smaller than and is positioned between outer cartridge cylinder 11 and outer baffle cylinder 13. Outer baffle cylinder 13 is attached to and contiguous with central rod 18.

Additionally, attachment cradle 16 is contiguous with, and is a superior extension of outer baffle cylinder 13. Cylinders 12 and 13 are machined to a tight tolerance to allow reciprocal movement of outer baffle cylinder 13 between outer cartridge cylinder 11 and inner baffle cylinder 12. This arrangement allows for only one path for liquids to travel through the microneedle cartridge apparatus 10. Liquid must move down between outer cartridge cylinder 11 and outer baffle cylinder 13, then upward between outer baffle cylinder 13 and inner baffle cylinder 12, then downward between inner baffle cylinder 12 and central rod 18. This path includes two 180 degree turns that interface directly with absorbent material gasket 21 at each turn, and this convoluted path prevents liquids from traversing through the microneedle cartridge apparatus into the nose cone apparatus and deeper into the reciprocal piston rod chamber.

The foregoing description has been presented and is intended for the purposes of illustration and description. It is not intended to be exhaustive nor limit the invention to the above teachings. The embodiments were chosen and described in order to best explain the principles of the invention and its practical application and to enable others skilled in the art to best utilize the invention in various embodiments and with various modifications as are suited to the particular use contemplated. Numerous other changes, substitutions, variations, alterations, and modifications may be ascertained to one skilled in the art. Therefore, it is intended that the invention not be limited to the particular embodiments disclosed for carrying out the invention.

What is claimed is:

1. A microneedle cartridge comprising
   a first cylinder component comprising an upper cylindrical section forming an outer cartridge cylinder, a lower cylindrical section of smaller radius than the upper cylindrical section forming a connection cylinder for connecting the cartridge to a microneedling device, and an inner baffle cylinder section; and
   a second cylinder component comprising an outer baffle cylinder having an upper platform for holding a microneedle array and a connecting rod extending downward from the platform;
   wherein the first and second cylinder components are concentric, the outer baffle cylinder surrounds the inner baffle cylinder, and the cylinders are dimensioned to a close fit that permits reciprocal movement of the outer baffle cylinder between the outer cartridge cylinder and the inner baffle cylinder; and
   a piston rod attachment cradle comprising an inverted cup configured to receive a polymer piston rod and housing and provide a shroud over the piston rod housing.

2. The cartridge of claim 1, further including fabric gaskets treated with an antimicrobial solution, located at the interface between the inner baffle cylinder and the inner cylinder and at the interface between the inner cylinder and the outer cylinder.

3. The cartridge of claim 1, further including a fabric gasket treated with an antimicrobial solution, located around the connecting rod at an uppermost position inside the connection cylinder.

4. The cartridge of claim 1 further including a fabric gasket treated with an antimicrobial solution, located at a floor of the inverted cup piston rod attachment cradle.

5. The microneedle cartridge assembly of claim 2, further including a detachable metal nose cone covering the cartridge when in place on the microneedling device.

* * * * *